(12) United States Patent
Smothers

(10) Patent No.: US 8,524,286 B2
(45) Date of Patent: Sep. 3, 2013

(54) PLANT EXTRACTION METHOD AND COMPOSITIONS

(75) Inventor: Donald L. Smothers, Terrell, TX (US)

(73) Assignee: Nerium Biotechnology, Inc., San Antonio, TX (US)

( * ) Notice: Subject to any disclaimer, the term of this patent is extended or adjusted under 35 U.S.C. 154(b) by 14 days.

(21) Appl. No.: 12/578,436

(22) Filed: Oct. 13, 2009

(65) Prior Publication Data

US 2010/0092585 A1   Apr. 15, 2010

Related U.S. Application Data

(60) Provisional application No. 61/105,133, filed on Oct. 14, 2008.

(51) Int. Cl.
*A61K 36/00* (2006.01)

(52) U.S. Cl.
USPC ......................................................... 424/725

(58) Field of Classification Search
USPC ......................................................... 424/725
See application file for complete search history.

(56) References Cited

U.S. PATENT DOCUMENTS

| | | | |
|---|---|---|---|
| 4,735,935 A | 4/1988 | McAnalley |
| 4,851,224 A | 7/1989 | McAnalley |
| 4,917,890 A | 4/1990 | McAnalley |
| 4,957,907 A | 9/1990 | McAnalley |
| 4,959,214 A | 9/1990 | McAnalley |
| 4,966,892 A | 10/1990 | McAnalley |
| 5,135,745 A | 8/1992 | Ozel |
| 6,565,897 B2 | 5/2003 | Selvaraj et al. |
| 7,402,325 B2 | 7/2008 | Addington |
| 2006/0188585 A1 | 8/2006 | Panosyan et al. |
| 2006/0205679 A1 | 9/2006 | Streeper et al. |
| 2007/0154573 A1 | 7/2007 | Rashan et al. |

FOREIGN PATENT DOCUMENTS

| | | |
|---|---|---|
| EP | 1 803 461 A1 | 7/2007 |
| WO | WO 00/16793 A1 | 3/2000 |

OTHER PUBLICATIONS

Reynolds. Aloes:The Genus Aloe. CRC Press. 2004. pp. 218-219.*
Dubin. Micacle Food Cures From the Bible. Penguin. 1998. 1 page.*
Manna et al. Oleandrin Suppresses Activation of Nuclear Transcription Factor-kB, Activator Protein-1, and c-Jun Nh2-Terminal. Cancer Research. 60. 3838-3847. Jul. 15, 2000.*
wikipedia.org. Sublingual Administration. Retrieved from the internet. <http://en.wikipedia.org/wiki/Sublingual_administration>. pp. 1-2. Retrieved on May 6, 2011.*
International Search Report and Written Opinion dated Jan. 13, 2010 for International Application No. PCT/US2009/060523, filed Oct. 13, 2009.
Office Action dated Jan. 21, 2012 (and English translation thereof), issued in Chinese Application No. 200980140777.5 filed Oct. 13, 2009.
Office Action dated Jul. 31, 2012, issued in Chinese Application No. 200980140777.5 filed Oct. 13, 2009.
Notice of Allowance dated Feb. 4, 2013, issued in Chinese Application No. 200980140777.5 filed Oct. 13, 2009.
Vazquez et al. Antiinflammatory activity of extracts from Aloe vera gel, J. Ethnopharmacol., 1996, 55(1):69-75.
Office Action dated May 28, 2013, issued in Russian Application No. 2011113151, filed Oct. 13, 2009.

* cited by examiner

*Primary Examiner* — Patricia Leith
(74) *Attorney, Agent, or Firm* — Knobbe Martens Olson & Bear LLP

(57) ABSTRACT

The present invention pertains to methods of extracting cardiac glycosides from cardiac glycoside containing plant material, such as *Nerium oleander*, through use of aloe. It further provides for compositions resulting from such extractions, pharmaceutical compositions, cosmetic compositions, and methods of treating skin conditions.

30 Claims, No Drawings

PLANT EXTRACTION METHOD AND COMPOSITIONS

CROSS-REFERENCE TO RELATED APPLICATIONS

This application claims the benefit of U.S. Provisional Application No. 61/105,133, filed on Oct. 14, 2008, which is incorporated herein by reference in its entirety.

FIELD OF THE INVENTION

The present invention pertains to methods of extracting materials from biological sources, and particularly from plant matter for cosmetic and medicinal applications.

DESCRIPTION OF THE RELATED ART

Biological sources have provided the bases for medicines and cosmetics from the earliest days of mankind. Most such sources have been plants, which initially were used as is. Oftentimes, however, it is desirable to extract materials from plants, as for example when the desired material constitutes only a small proportion of a given plant, or when the material occurs in the presence of other, undesirable constituents.

Glycosides represent an important class of compounds extracted from plant sources. Cardiac glycosides, for example, are glycosylated steroids, i.e., steroids conjugated to a carbohydrate moiety. Examples of cardiac glycosides include those useful in the production of such drugs as digoxin and digitoxin. An important class of glycosides comes from the genus *Nerium*, which includes such species as *Nerium indicum, Nerium odorum*, and *Nerium oleander*, the last being the oleander plant native to Asia and the Mediterranean littoral and now found also in parts of the United States. The various *Nerium* species afford such glycosides as oleandrin, which finds extensive use in medicine.

Extraction of cardiac glycosides from *Nerium oleander* facilitates their use clinically by allowing administration of compositions of known potency and purity. Previous methods of extracting these glycosides have employed hot water, as described in U.S. Pat. Nos. 5,135,745 and 6,565,897, as well as U.S. Patent Publication No. 20060188585, each of which is hereby incorporated by reference in its entirety. Owing to the large lipophilic steroidal moiety, however, oleandrin has poor aqueous solubility, which limits the effectiveness of aqueous extraction. Furthermore, plants generally have waxy cuticles surrounding their exterior surfaces to minimize desiccation. This waxy cuticle not only limits the egress of water from the plant to the exterior, but also the ingress of water from the exterior into the plant, and thus further impedes efficient aqueous extraction of the desired cardiac glycosides. Also, the desired cardiac glycosides can hydrolyze or otherwise decompose on long exposure to hot water.

One solution to these problems has been to perform the extraction not with pure water, but with a mixture of water and a water-miscible alcohol, such as methanol or ethanol, as described in U.S. Patent Publication No., 20070154573, which is hereby incorporated by reference in its entirety. Use of aqueous alcohol increases both the penetration of the extraction solvent into the interior of the plant and the solubility of the cardiac glycosides to some extent. More recently, U.S. Pat. No. 7,402,325, which is hereby incorporated by reference in its entirety, has described use of supercritical $CO_2$ as extracting higher yields of desired product from powdered oleander leaves. Extraction with supercritical $CO_2$ necessitates use of high pressure apparatus (above ca. 100 atmospheres), with all of its attendant hazards.

Accordingly, a need exists for a way to extract oleandrin and other cardiac glycosides more efficiently from various plant species such as *Nerium* without use of excessive heat or high pressure apparatus.

SUMMARY OF THE INVENTION

The present invention provides a method to extract cardiac glycosides from a cardiac glycoside-containing plant species, such as a *Nerium* species, through use of aloe, such as that derived from *Aloe vera*. It further provides compositions resulting from such extraction.

Specifically, it provides a method of performing an extraction of plant material derived from a cardiac glycoside-containing plant species, such as a species from the genus *Nerium*, comprising agitating the plant material in aloe mucilage and separating the extract from any remaining solid material.

The extraction method optionally involves heating the solution from about 40° C. to about 100° C., optionally including use of extraction adjuvants such as alcohols, ketones, and esters.

An embodiment provides a method of extracting cardiac glycosides comprising intermixing a cardiac glycoside plant species with aloe under conditions selected to form an extraction mixture.

An embodiment further provides conditioning the extraction mixture under conditions selected to extract cardiac glycosides from the cardiac glycoside plant species to form a conditioned extraction mixture, wherein the conditioned extraction mixture comprises residual cardiac glycoside plant species and a cardiac glycoside aloe mixture.

An embodiment further provides separating at least a portion of the cardiac glycoside aloe mixture from the residual cardiac glycoside plant species to form a cardiac glycoside aloe extract, where the cardiac glycoside aloe extract comprises cardiac glycosides extracted from a cardiac glycoside plant species, and where the cardiac glycoside aloe extract is substantially free of the residual cardiac glycoside plant species.

In some embodiments the cardiac glycoside plant species belongs to a family selected from Apocynaceae, Brassicaceae, Plantaginaceae, Ruscaceae, or Hyacinthaceae.

In some embodiments the cardiac glycoside plant belongs to the species *Nerium indicuim* or *Nerium oleander*.

In some embodiments the conditioning comprises heating the extraction mixture to a temperature in the range of about 40° C. to about 100° C. to form the conditioned extraction mixture.

In some embodiments the conditioning comprises heating the extraction mixture for a heating time in the range of about 1 to about 10 hours.

In some embodiments the separating comprises subjecting the conditioned extraction mixture to a separation method selected from the group consisting of filtration, centrifugation, and decanting.

In some embodiments the extraction mixture comprises an amount of the cardiac glycoside plant species in the range of about one part to about 50 parts by weight and an amount of the aloe in the range of about one part to about 100 parts by weight, based on the total weight of extraction mixture.

In some embodiments the extraction mixture comprises an adjuvant selected from the group consisting of alcohols, ketones, and esters.

An embodiment provides a cardiac glycoside aloe composition, comprising aloe and at least one cardiac glycoside.

In some embodiments, the cardiac glycoside is a cardiac glycoside aloe extract from a cardiac glycoside plant species.

In some embodiments, the cardiac glycoside aloe composition is a cardiac glycoside aloe extract wherein the cardiac glycoside plant species is *Nerium oleander*.

An embodiment provides pharmaceutical compositions comprising aloe, at least one cardiac glycoside and a pharmaceutically acceptable carrier. Another embodiment provides cosmetic compositions comprising aloe, at least one cardiac glycoside and a dermal agent.

In certain embodiments, a method of treatment is provided comprising identifying a subject having a skin condition and applying an effective amount of the pharmaceutical composition comprising aloe and at least one cardiac glycoside to the skin of a subject to thereby treat the skin condition.

In certain embodiments the skin condition is selected from the group consisting of abscesses, acne, actinic keratosis, age spots, liver spots, burns, sunburn, heat burn, radiation burn, cold sores, corns, eczema, psoriasis, ringworm, scabies, skin cancers, basal skin cancer, squamous skin cancer, melanoma skin cancer, skin tags, and warts.

These and other embodiments are described in greater detail below.

DETAILED DESCRIPTION OF THE PREFERRED EMBODIMENTS

An embodiment provides a method of extracting cardiac glycosides, comprising intermixing a cardiac glycoside plant species with aloe under conditions selected to form an extraction mixture.

Examples of cardiac glycoside plant species include those in the family Apocynaceae (dogbane), particularly in the genera *Nerium, Strophanthus, Apocynum, Thevetia*, and *Catharanthus*, the family Brassicaceae, particularly in the genus *Chemanthus*, the family Plantaginaceae, particularly in the genus *Digitalis*, the family Ruscaceae, particularly in the genus *Convallaria*, and in the family Hyacinthaceae, particularly in the genus *Urginea*.

Examples of particular cardiac glycoside plant species include *Nerium oleander, Thevetia nerifolia, Digitalis purpurea, Digitalis lanate, Convallaria majalis, Urginea maritima, Urginea indica, Strophanthus gratus, Apocynum cannabinum, Chemanthus cheiri*.

The term "aloe" refers to a genus of plants native to Africa and comprising about 400 species, including *Aloe arborescens, Aloe aristata, Aloe dichotoma, Aloe nyeriensis, Aloe varvegata, Aloe wildii*, and *Aloe barbadensis miller*.

In some embodiments, the conditions selected to form an extraction mixture comprise mixing aloe with the leaves and stems of a cardiac glycoside plant species that are optionally cut into pieces, milled, or powdered to facilitate the extraction.

In some embodiments, the extraction mixture comprises an amount of cardiac glycoside plant species in the range of about one part to about 50 parts by weight and an amount of aloe in the range of about one part to about 100 parts by weight, based on total weight of the extraction mixture.

An embodiment further provides conditioning the extraction mixture under conditions selected to extract cardiac glycosides from cardiac glycoside plant species to form a conditioned extraction mixture, wherein the conditioned extraction mixture comprises residual cardiac glycoside plant species and a cardiac glycoside aloe mixture.

Examples of conditioning the extraction mixture under conditions selected to extract cardiac glycosides from cardiac glycoside plant species, include heating the extraction mixture, agitating the extraction mixture, and heating the extraction mixture with agitation.

In some embodiments, conditioning the extraction mixture under conditions selected to extract cardiac glycosides from cardiac glycoside plant species comprises heating the extraction mixture to a temperature in the range of about 40° C. to about 100° C. to form a conditioned extraction mixture.

In some embodiments, conditioning the extraction mixture under conditions selected to extract cardiac glycosides from cardiac glycoside plant species comprises heating the extraction mixture for a time in the range of about 1 to about 10 hours to form a conditioned extraction mixture.

In some embodiments, a conditioned extraction mixture comprises a mixture where a portion of the cardiac glycosides from the cardiac glycoside plant species are extracted into the aloe present in the mixture. Thus, the result of conditioning is to form a conditioned extraction mixture that contains residual cardiac glycoside plant species and a cardiac glycoside aloe mixture that contains both aloe and the cardiac glycoside(s) extracted into the aloe from the cardiac glycoside plant species.

An embodiment further provides separating at least a portion of the cardiac glycoside aloe mixture from the residual cardiac glycoside plant species to form a cardiac glycoside aloe extract.

Those skilled in the art will appreciate that the cardiac glycoside aloe extract may contain, in addition to cardiac glycoside(s), other components extracted by the aloe from the cardiac glycoside plant species, such as, for example, polysaccharide(s).

Examples of separating at least a portion of the cardiac glycoside aloe mixture from the residual cardiac glycoside plant species include filtration, separation, and decanting.

In some embodiments, the cardiac glycoside aloe extract comprises cardiac glycosides extracted from the cardiac glycoside plant species.

In some embodiments, the cardiac glycoside aloe extract is substantially free of the residual cardiac glycoside plant species.

In some embodiments, the extraction mixture comprises an adjuvant selected from the group consisting of alcohols, ketones, and esters.

A further embodiment provides a cardiac glycoside aloe composition, comprising aloe and at least one cardiac glycoside.

In some embodiments, the cardiac glycoside is a cardiac glycoside aloe extract from a cardiac glycoside plant species.

In some embodiments, the cardiac glycoside aloe composition is a cardiac glycoside aloe extract wherein the cardiac glycoside plant species is *Nerium oleander*.

An embodiment provides pharmaceutical compositions comprising a cardiac glycoside aloe composition comprising aloe, at least one cardiac glycoside and a pharmaceutically acceptable carrier. Examples of pharmaceutically acceptable carriers include dermal agents as well as the carriers known to those skilled in the pharmaceutical arts for inclusion in orally administrable forms such as pills, capsules and sublingual compositions.

Examples of dermal agents include cosmetic compositions and various ingredients known to those skilled in the art of formulating them, such as, for example, an oily ointment, an aqueous ointment, a cream, a lotion (e.g., a cosmetic lotion, a face lotion), an emulsion, a pack, a soap, a face wash, a makeup (a body makeup, a face makeup) and combinations thereof.

An embodiment provides pharmaceutical compositions comprising a cardiac glycoside aloe extract from a cardiac glycoside plant species and a dermal agent.

In certain embodiments, a method of treatment is provided comprising identifying a subject having a skin condition and applying an effective amount of the pharmaceutical composition (e.g., comprising aloe and at least one cardiac glycoside) to the skin of a subject to thereby treat the skin condition. In this context, the treatment of the skin condition does not necessarily imply medical treatment, and thus for example may include providing a benefit typically associated with the application of a cosmetic, such as soothing, softening or moisturizing the skin and/or hair.

Examples of a "skin condition" include abscesses, dry skin, sun-damaged skin, aging skin, acne, actinic keratosis, age spots, liver spots, burns, sunburn, heat burn, radiation burn, cold sores, corns, eczema, psoriasis, ringworm, scabies, skin cancers, basal skin cancer, squamous skin cancer, melanoma skin cancer, skin tags, and/or warts.

An embodiment provides a method of extracting compounds, including in particular medicinally valuable glycosides, from material derived from a cardiac glycoside-containing plant species. Cardiac glycoside-containing plant species are found in the family Apocynaceae (dogbane), particularly in the genera *Nerium, Strophanthus, Apocynum, Thevetia*, and *Catharanthus*, the family Brassicaceae, particularly in the genus *Chemanthus*, the family Plantaginaceae, particularly in the genus *Digitalis*, the family Ruscaceae, particularly in the genus *Convallaria*, and in the family Hyacinthaceae, particularly in the genus *Urginea*.

Particular species include *Nerium oleander, Thevetia nerifolia, Digitalis purpurea, Digitalis lanate, Convallaria majalis, Urginea maritima, Urginea indica, Strophanthus gratus, Apocynum cannabinum, Chemanthus cheiri*. In a preferred embodiment, the material is derived from *Nerium oleander*, the well-known oleander plant.

The applicant has found that use of aloe mucilage enhances the extraction efficiency of medicinally useful extracts from cardiac glycoside-containing plant species, such as those cited above. The term "aloe" refers to a genus of plants native to Africa and comprising about 400 species, including *Aloe arborescens, Aloe aristata, Aloe dichotoma, Aloe nyeriensis, Aloe varvegata, Aloe wildii*, and *Aloe barbadensis miller*, while "mucilage" refers to the mucilageneous gel obtained from within their leaves.

In use, mucilage derived from an *Aloe* species, such as *Aloe barbadensis miller*, is obtained by methods well-known to those skilled in the art. For example, U.S. Pat. No. 4,957,907, which is hereby incorporated by reference in its entirety, describes in detail one procedure for extracting aloe plant material.

The aloe is then mixed with plant material in a manner selected to extract cardiac glycosides. For example, the mucilage obtained from an aloe plant is then mixed with plant material from a *Nerium* species, such as *Nerium oleander* in a ratio of about 1-100 parts of aloe to one of oleander on a weight basis, and preferably 5-20 parts of aloe to one of oleander, and most preferably about nine parts of aloe to one of oleander, although the exact proportions are not critical. The plant material can include leaves and stems that are optionally cut into pieces, milled, or powdered to facilitate the extraction. If desired, the plant material can be dried before extraction and can be powdered to increase the surface area.

In an embodiment, the vessel is then heated to with agitation to about 40° C. to about 100° C., for about one to 10 hours, but the time is not critical. The time to achieve a desired degree of extraction can be readily determined by those skilled in the art. Similarly, agitation can be accomplished by shaking, vortexing, sonicating, or other method, the choice of which is not critical.

In a preferred embodiment, the vessel is heated with agitation to about 80° C. for about five hours. The vessel is then cooled to room temperature, and the solids separated from the extract by a suitable method, such as settling, filtering, decanting, screening, or centrifuging, or some combination of these separation methods.

If desired, the resulting effluent can then be filtered through 1 micron screen, followed by an optional further filtration through a screen with openings between about 0.5 and 1 micron in diameter.

In one embodiment, the extraction is performed by immersing material from a cardiac glycoside-containing plant species, such as *Nerium oleander*, in a vessel containing the aloe-containing extraction solution. The plant material can include leaves and stems that are optionally cut into pieces to facilitate extraction. If desired, the plant material is dried before extraction, and can optionally also be powdered to increase the surface area.

Similarly, the extraction can be performed at any temperature above the freezing point of the solution. In one embodiment, the extraction is performed at room temperature, but if desired, an elevated temperature can also be used, as the temperature is not critical.

Furthermore, if desired, an extraction adjuvant can be added to the solution. Such adjuvant can be an organic alcohol, ether, ketone, or ester. Examples include methanol, ethanol, n- and iso-propanol, methoxyethanol, 2-butoxyethanol, diethyl ether, acetone, butanone, and ethyl acetate, and mixtures of such solvents.

After extraction has proceeded to the desired extent, the extract can be separated from the remaining plant material by a variety of methods, including filtration, centrifugation, and decantation, all methods well-known in the art, to produce the aloe-based extract.

The resulting aloe-based extract can be used medicinally either as prepared, or can be further treated if desired, for example by evaporation of some of the solution either at atmospheric or reduced pressure, and either at room temperature or an elevated temperature. Alternatively, if desired, the extract composition can be freeze-dried, or spray-dried, or subjected to liquid-liquid extraction.

The term "pharmaceutical composition" refers to a mixture of a cardiac glycoside aloe extract as described herein with other chemical components, such as diluents or carriers. The pharmaceutical composition facilitates application or administration of the aloe extract to an organism. Multiple techniques of administering a compound exist in the art including, but not limited to, oral, injection, aerosol, parenteral, and topical application or administration. The term "pharmaceutical composition" as used herein includes cosmetic compositions and nutraceutical compositions, which are not intended for use in the treatment of a particular disease or condition, and thus the term "pharmaceutical" in this context does not necessarily imply that the composition contains an amount or type of cardiac glycoside aloe extract that would render the composition useful as a drug.

The term "carrier" refers to a chemical compound that facilitates the incorporation of a compound into cells or tissues. For example dimethyl sulfoxide (DMSO) is a commonly utilized carrier as it facilitates the uptake of many organic compounds into the cells or tissues of an organism.

The term "diluent" refers to chemical compounds diluted in water that will dissolve the aloe extract as well as stabilize the biologically active form. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

The term "physiologically acceptable" defines a carrier or diluent that does not abrogate the biological activity and properties of the aloe extract.

The pharmaceutical compositions described herein can be administered to a human patient per se, or in pharmaceutical compositions where they are mixed with other active ingredients, as in combination therapy, or suitable carriers or excipient(s). Techniques for formulation and administration of the compounds of the instant application may be found in "Remington's Pharmaceutical Sciences," Mack Publishing Co., Easton, Pa., 18th edition, 1990.

Suitable routes of application and/or administration may, for example, include topical (e.g., in the form a a cosmetic composition or hair care product), oral, sublingual, rectal, transmucosal, or intestinal administration; parenteral delivery, including intramuscular, subcutaneous, intravenous, intramedullary injections, as well as intrathecal, direct intraventricular, intraperitoneal, intranasal, or intraocular injections.

The pharmaceutical compositions described herein may be manufactured in a manner that is itself known, e.g., by means of conventional mixing, dissolving, granulating, dragee-making, levigating, emulsifying, encapsulating, entrapping or tabletting processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the intended use (e.g., cosmetic versus treatment of a disease or condition), and the route of application or administration chosen. Any of the well-known techniques, carriers, and excipients may be used as suitable and as understood in the art; e.g., in Remington's Pharmaceutical Sciences, above.

For injection, the aloe extract may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the aloe extract can be formulated readily by combining with pharmaceutically acceptable carriers well known in the art. Such carriers enable the aloe extract to be formulated as tablets, pills, sublingual compositions, dragees, capsules, liquids, gels, syrups, slurries, suspensions and the like, for oral ingestion by a patient to be treated. Pharmaceutical preparations for oral use can be obtained by mixing one or more solid excipients with the aloe extract described herein, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are typically provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the aloe extract in admixture with filler such as lactose, binders such as starches, and/or lubricants such as talc or magnesium stearate and, optionally, stabilizers. In soft capsules, the aloe extract may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

Alternatively, the active ingredient may be in powder form for constitution with a suitable vehicle, e.g., sterile pyrogen-free water, before use.

An example of a pharmaceutical carrier for hydrophobic aloe extracts is a cosolvent system comprising benzyl alcohol, a nonpolar surfactant, a water-miscible organic polymer, and an aqueous phase. A common cosolvent system used is the VPD co-solvent system, which is a solution of 3% w/v benzyl alcohol, 8% w/v of the nonpolar surfactant Polysorbate 80™, and 65% w/v polyethylene glycol 300, made up to volume in absolute ethanol. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of POLYSORBATE 80™; the fraction size of polyethylene glycol may be varied; other biocompatible polymers may replace polyethylene glycol, e.g., polyvinyl pyrrolidone; and other sugars or polysaccharides may substitute for dextrose.

Alternatively, other delivery systems for hydrophobic aloe extracts may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the aloe extract may be delivered using a sustained-release system. Various sustained-release materials have been established and are well known by those skilled in the art. Sustained-release capsules may, depending on their chemical nature, extend the release of the aloe extract for a few hours up to a few weeks.

Pharmaceutical compositions suitable for use include compositions where the aloe extract is contained in an amount effective to achieve its intended purpose. More specifically, a therapeutically effective amount means an amount of aloe extract effective to prevent, alleviate or ameliorate symptoms of disease or prolong the survival of the subject being treated. Determination of a therapeutically effective amount is well within the capability of those skilled in the art, especially in light of the detailed disclosure provided herein.

The exact formulation, route of administration and dosage for the pharmaceutical compositions can be chosen by the individual physician in view of the patient's condition. (See e.g., Fingl et al. 1975, in "The Pharmacological Basis of Therapeutics", Ch. 1 p. 1). Typically, the dose range of the composition administered to the patient can be from about 0.5 to 1000 mg/kg of the patient's body weight. The dosage may be a single one or a series of two or more given in the course of one or more days, as is needed by the patient. Note that for water and $CO_2$-based plant extracts mentioned in the present disclosure, human dosages for treatment of at least some condition have been established. Thus, in most instances, those same dosages may be used for the aloe extracts, or dosages that are between about 0.1% and 500%, more preferably between about 25% and 250% of the established human dosage. Where no human dosage is established, a suitable human dosage can be inferred from $ED_{50}$ or $ID_{50}$ values, or other appropriate values derived from in vitro or in vivo studies, as qualified by toxicity studies and efficacy studies in animals.

The amount of aloe extract administered will generally be dependent on the subject being treated, on the subject's weight, the severity of the affliction, the manner of administration and the judgment of the prescribing physician.

EXAMPLES

Example 1

An extraction mixture was created as follows: The dried leaves and stems of a cardiac glycoside plant species comprising *Nerium oleander* (100 g) were milled to a fine powder, weighed into a glass container and intermixed with aloe comprised of *Aloe barbadensis* leaf juice (900 g) that had been processed to a liquid with a maximum anthraquinone (aloin and/or aloe emodin) content of 1 ppm, pH of 3.7-4.1, and containing 0.1% potassium sorbate.

The extraction mixture was agitated until homogeneous, and the container with the extraction mixture was placed into a temperature controlled water bath with the water level in the water bath maintained at 60%-80% of the level of the extraction mixture in the container. The water bath was heated to 80-85° C. and held at that temperature for five hours with no agitation. The conditioned extraction mixture was then covered and allowed to cool.

After the conditioned extraction mixture cooled, a portion of the cardiac glycoside aloe mixture was separated from the residual cardiac glycoside plant species as follows: The cardiac glycoside aloe mixture at the top of the conditioned extraction mixture was decanted. The cardiac glycoside aloe mixture was then separated from the residual cardiac glycoside plant species by straining. The cardiac glycoside aloe extract liquid was then combined and agitated until homogeneous.

The homogenous cardiac glycoside aloe extract was then filtered through a medium of approximately 1 micron porosity, followed by a second filtration through a medium of 0.5-1.0 micron porosity, and the resulting cardiac glycoside aloe extract (substantially free of the residual cardiac glycoside plant species) was stored in a sealed glass container at ambient temperature.

Example 2

A pharmaceutical composition was created as follows: A cardiac glycoside aloe extract (substantially free of the residual cardiac glycoside plant species) prepared as described in Example 1 was combined with a dermal agent in a ratio of 4 parts by weight of cardiac glycoside aloe extract to 1 part by weight of dermal agent, based on the total weight of the pharmaceutical composition. The dermal agent contained Glycerin, Methyl Sulfonyl Methane, *Oryzo Sativa* (Rice Bran) Oil, *Ricinus Communis* (Castor) Oil, Glyceryl Stearate, Styrene/Acrylates Copolymer, PEG-100 Stearate, Cetyl Alcohol, Dimethicone, Carbomer, Caprylyl Glycol, Glycerin, Glyceryl Caprylate, Phenylpropanol, Methyl Paraben, Tocopherol (Vitamin E), and Fragrance.

Example 3

Subjects were identified who suffered from age/liver spots. Each subject's lesion color was determined on a four-grade color scale ranging from: black, dark brown, light brown, to same color as surrounding pigment (age spots no longer visible). 14 subjects used the pharmaceutical composition prepared as described in Example 2 to spot treat their age/liver spots. 6 subjects used a pharmaceutical composition containing a cream made with a hot-water *Nerium oleander* extract to treat their age/liver spots.

After treatment, the results were measured according to the following scale: complete healing (complete disappearance of age spots), good (3 grades decrease in lesion color), partial (2 grades decrease in lesion color), or poor (1 grade decrease or no change in lesion color).

Out of the 14 subjects who used the pharmaceutical composition prepared as described in Example 2, 7 subjects, or 50%, reported either complete healing or 3 grades of decrease in lesion color. Out of the 6 subjects who used the pharmaceutical composition containing a cream made with a hot-water extract, 4 subjects, or 67%, reported either complete healing or 3 grades of decrease in lesion color.

Example 4

Subjects were identified who suffered from acne. When 13 subjects used a pharmaceutical composition prepared as described in Example 2 to treat the acne, 9 subjects, or 70%, found the product to be as good as or better than Proactive Renewing Cleanser, a face cleanser known for use by persons having acne and commercially available from Guthy-Renker, LLC.

Example 5

Subjects were identified who suffered from sunburn. When 16 of the subjects used a pharmaceutical composition prepared as described in Example 2 to treat the sunburn, 13 subjects, or 85%, found the product to be as good as or better than a commercially available sunburn product (Aloe Vera's After Sun Body Lotion with Tea Tree Oil).

Example 6

A pharmaceutical composition was created as follows: A cardiac glycoside aloe extract (substantially free of the residual cardiac glycoside plant species) as described in Example 1 was mixed with a dermal agent in the manner described in Example 2. The dermal agent contained L-Lysine, Styrene/Acrylates Copolymer, Glycerin, *Oryzo Sativa* (Rice Bran) Oil, Glyceryl Stearate, Cetyl Alcohol, Dimethicone, Carbomer, C14-22 Alcohols and C12-20 Alkyl Glucoside, *Olea Europaea* (Olive) Leaf Extract, Caprylyl Glycol, Glycerin, Glyceryl Caprylate, Phenylpropanol, Methyl Paraben, Ascorbic Acid, Citric Acid, Lactic Acid, Glycerin, Water, *Eugenia Caryophyllus* (Clove) Flower Oil, and Camphor.

Example 7

Subjects were identified who suffered from cold sores. When 19 of the subjects with cold sores applied a pharmaceutical composition prepared as described in Example 6, the following results were noted:

Of the 14 subjects who had previously used other cold sore treatments, 4 subjects, or 29%, found that it worked as well as the previous treatments and 8 subjects, or 57%, found that it worked better than other previously used products.

When 19 subjects with cold sores applied the pharmaceutical composition, 12 subjects, or 63%, found that the pharmaceutical composition decreased the appearance/redness of the cold sore compared with previous product experiences.

It will be understood by those of skill in the art that numerous and various modifications can be made without departing from the spirit of the present invention. Therefore, it should be clearly understood that the various embodiments of the present invention described herein are illustrative only and not intended to limit the scope of the present invention.

What is claimed is:

1. A cardiac glycoside aloe composition comprising a *Nerium oleander* aloe extract, wherein said extract is prepared by extracting *Nerium oleander* with aloe to create an extraction mixture comprising liquid and solid material and separating the solid material from the liquid material; wherein said liquid material is the *Nerium oleander* aloe extract.

2. A pharmaceutical composition comprising the cardiac glycoside aloe composition of claim 1, and further comprising a pharmaceutically acceptable carrier.

3. The pharmaceutical composition of claim 2 in pill, sublingual or cosmetic form.

4. The pharmaceutical composition of claim 2 wherein the pharmaceutically acceptable carrier comprises a dermal agent.

5. A method of treating a skin condition, comprising administering an effective amount of the composition of claim 4 to a subject in need thereof; wherein said skin condition is selected from the group consisting of abscesses, dry skin, sun-damaged skin, aging skin, acne, actinic keratosis, age spots, liver spots, burns, sunburn, heat burn, radiation burn, cold sores, corns, eczema, psoriasis, ringworm, scabies, skin tags, warts and combinations thereof.

6. A method of applying a cosmetic, comprising applying the cardiac glycoside aloe composition of claim 1 to the skin of a subject.

7. A method of applying a cosmetic, comprising:
identifying a subject in need of cosmetic application; and
applying a cosmetically effective amount of the cardiac glycoside aloe composition of claim 1 or claim 4 to the skin of said subject, wherein
said subject has a skin condition selected from the group consisting of abscesses, dry skin, sun-damaged skin, aging skin, acne, actinic keratosis, age spots, liver spots, burns, sunburn, heat burn, radiation burn, cold sores, corns, eczema, psoriasis, ringworm, scabies, skin tags, warts and combinations thereof.

8. A method of extracting cardiac glycosides, comprising:
mixing *Nerium oleander* having cardiac glycosides with aloe to form an extraction mixture and
separating the extract from the solid *Nerium oleander* plant material.

9. The method of claim 8, wherein the method further comprises heating said extraction mixture for about 1 to about 10 hours.

10. The method of claim 8, wherein the method further comprises heating said extraction mixture to a temperature in the range of about 40° C. to about 100° C.

11. The method of claim 8 wherein said separating comprises filtering, centrifuging or decanting.

12. The method of claim 8, wherein the extraction mixture comprises *Nerium oleander* in a range of about one part to about 50 parts by weight and wherein the extraction mixture comprises aloe in a range of about one part to about 100 parts by weight.

13. The method of claim 8, wherein the extraction mixture comprises a solvent selected from the group consisting of alcohols, ketones, ethers, esters and mixtures thereof.

14. The method of claim 13, wherein said solvent is selected from the group consisting of methanol, ethanol, n-propanol, iso-propanol, methoxyethanol, 2-butoxyethanol, diethyl ether, acetone, butanone, ethyl acetate, and mixtures thereof.

15. A cardiac glycoside aloe composition comprising a cardiac glycoside aloe extract, wherein said cardiac glycoside aloe extract is prepared by extracting a plant with aloe to create an extraction mixture comprising liquid and solid material and separating the solid material from the liquid material, wherein said liquid material is the cardiac glycoside aloe extract and wherein said plant consists of a cardiac glycoside plant selected from *Digitalis purpurea, Digitalis lanate, Convallaria majalis, Urginea maritime, Urginea indica, Strophanthus gratus, Apocynum cannabinum, Cheiranthus cheiri* and *Nerium indicum*.

16. A pharmaceutical composition comprising the cardiac glycoside aloe composition of claim 15 and further comprising a pharmaceutically acceptable carrier.

17. The pharmaceutical composition of claim 16 in pill, sublingual or cosmetic form.

18. The pharmaceutical composition of claim 16 wherein the pharmaceutically acceptable carrier comprises a dermal agent.

19. A method of treating a skin condition, comprising administering an effective amount of the composition of claim 15 or claim 18 to a subject in need thereof; wherein said skin condition is selected from the group consisting of abscesses, dry skin, sun-damaged skin, aging skin, acne, actinic keratosis, age spots, liver spots, burns, sunburn, heat burn, radiation burn, cold sores, corns, eczema, psoriasis, ringworm, scabies, skin tags, warts and combinations thereof.

20. A method of applying a cosmetic, comprising applying the cardiac glycoside composition of claim 15 or claim 18 to the skin of a subject.

21. A method of applying a cosmetic, comprising:
identifying a subject in need of cosmetic application; and
applying a cosmetically effective amount of the cardiac glycoside composition of claim 15 or claim 18 to the skin of said subject, wherein
said subject has a skin condition selected from the group consisting of abscesses, dry skin, sun-damaged skin, aging skin, acne, actinic keratosis, age spots, liver spots, burns, sunburn, heat burn, radiation burn, cold sores, corns, eczema, psoriasis, ringworm, scabies, skin tags, warts and combinations thereof.

22. A method of extracting cardiac glycosides, comprising:
mixing a composition consisting of a cardiac glycoside plant and aloe to form an extraction mixture, separating the liquid extract from the solid cardiac glycoside plant material and collecting the liquid extract; wherein the cardiac glycoside plant is selected from *Digitalis purpurea, Digitalis lanate, Convallaria majalis, Urginea maritime, Urginea indica, Strophanthus gratus, Apocynum cannabinum, Cheiranthus cheiri* and *Nerium indicum*.

23. The method of claim 22, wherein the method further comprises heating said extraction mixture for about 1 to about 10 hours.

24. The method of claim 22, wherein the method further comprises heating said extraction mixture to a temperature in the range of about 40° C. to about 100° C.

25. The method of claim 22 wherein said separating comprises filtering, centrifuging or decanting.

26. The method of claim 22, wherein the extraction mixture comprises the cardiac glycoside plant in a range of about one part to about 50 parts by weight and wherein the extraction mixture comprises aloe in a range of about one part to about 100 parts by weight.

27. The method of claim 22, wherein the extraction mixture comprises a solvent selected from the group consisting of alcohols, ketones, ethers, esters and mixtures thereof.

28. The method of claim 27, wherein said solvent is selected from the group consisting of methanol, ethanol, n-propanol, iso-propanol, methoxyethanol, 2-butoxyethanol, diethyl ether, acetone, butanone, ethyl acetate and mixtures thereof.

29. The cardiac glycoside aloe composition of claim 1 further comprising polysaccharides.

30. The cardiac glycoside aloe composition of claim 15 further comprising polysaccharides.

* * * * *

UNITED STATES PATENT AND TRADEMARK OFFICE
CERTIFICATE OF CORRECTION

PATENT NO. : 8,524,286 B2  
APPLICATION NO. : 12/578436  
DATED : September 3, 2013  
INVENTOR(S) : Smothers Page 1 of 1

It is certified that error appears in the above-identified patent and that said Letters Patent is hereby corrected as shown below:

In the Specification

In column 2 at line 48, Change "Nerium indicuim" to --Nerium indicium--.

In column 3 at line 39, Change "Chemanthus," to --Cheiranthus,--.

In column 3 at line 44, Change "Thevetia nerifolia," to --Thevetia neriifolia,--.

In column 3 at line 45, Change "Digitalis lanate," to --Digitalis lanata,--.

In column 3 at line 47, Change "Chemanthus" to --Cheiranthus--.

In column 3 at lines 50-51, Change "Aloe varvegata," to --Aloe variegata,--.

In column 5 at line 31, Change "Chemanthus," to --Cheiranthus,--.

In column 5 at lines 35-36, Change "Thevetia nerifolia," to --Thevetia neriifolia,--.

In column 5 at line 36, Change "Digitalis lanate," to --Digitalis lanata,--.

In column 5 at line 38, Change "Chemanthus" to --Cheiranthus--.

In column 5 at line 47, Change "Aloe varvegata," to --Aloe variegata,--.

In column 5 at line 48, Change "mucilageneous" to --mucilaginous--.

In column 7 at line 24, Change "a a" to --a--.

In column 10 at line 6, Change "Oryzo Sativa" to --Oryza Sativa--.

In column 10 at lines 63-64, Change "Oryzo Sativa" to --Oryza Sativa--.

In the Claims

In column 12 at lines 29-30, In Claim 15, Change "Digitalis lanate," to --Digitalis lanata,--.

In column 12 at line 30, In Claim 15, Change "Urginea maritime," to --Urginea maritima,--.

In column 13 at line 2, In Claim 22, Change "Digitalis lanate," to --Digitalis lanata,--.

In column 13 at lines 2-3, In Claim 22, Change "Urginea maritime," to --Urginea maritima,--.

Signed and Sealed this  
Fifteenth Day of April, 2014

Michelle K. Lee  
*Deputy Director of the United States Patent and Trademark Office*